(12) United States Patent
Ishino et al.

(10) Patent No.: US 7,531,674 B2
(45) Date of Patent: May 12, 2009

(54) PROCESS FOR PRODUCING PROPYLENE OXIDE

(75) Inventors: Masaru Ishino, Sodegaura (JP); Hiroaki Abekawa, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 426 days.

(21) Appl. No.: 10/547,628

(22) PCT Filed: Mar. 4, 2004

(86) PCT No.: PCT/JP2004/002757

§ 371 (c)(1),
(2), (4) Date: Sep. 2, 2005

(87) PCT Pub. No.: WO2004/078739

PCT Pub. Date: Sep. 16, 2004

(65) Prior Publication Data

US 2006/0173200 A1 Aug. 3, 2006

(30) Foreign Application Priority Data

Mar. 6, 2003 (JP) .............................. 2003-059604

(51) Int. Cl.
*C07D 301/06* (2006.01)
(52) U.S. Cl. ...................... 549/533; 502/242
(58) Field of Classification Search .............. 549/531, 549/533; 502/242
See application file for complete search history.

(56) References Cited

U.S. PATENT DOCUMENTS

| 5,621,122 | A | 4/1997 | Saxton et al. |
| 6,114,551 | A | 9/2000 | Levin et al. |
| 6,350,888 | B1 | 2/2002 | Strebelle et al. |
| 6,500,311 | B1 * | 12/2002 | Sawyer ..................... 203/44 |

FOREIGN PATENT DOCUMENTS

| EP | 1 488 853 A1 | 12/2004 |
| EP | 1 489 075 A1 | 12/2004 |
| JP | 10-25285 A | 1/1998 |
| JP | 10225285 | 8/1998 |
| WO | 99/14208 A1 | 3/1999 |

OTHER PUBLICATIONS

Wu et al., Chem Commun., 2001, 897-898.*
Heisei 13 nendo Jisedai Kagaku Process Gijutu Kaihatu Non-halogen Kagaku Process Gijitu Kaihatu Seika Houkokusho, Japan Chemical Innovation Institute, FY2001 Annual Report, pp. 168-209, (Mar. 2002).
Heisei 14 nendo Jisedai Kagaku Process Gijutu Kaihatu Non-halogen Kagaku Process Gijitu Kaihatu Seika Houkokusho, "Chapter 3 Development of a new synthetic method of expoxides," Japan Chemical Innovation Institute, FY2002 Annual Report, pp. 152-180, (Mar. 2003).
Clerici et al. "Synthesis of Propylene Oxide from Propylene and Hydrogen Peroxide Catalyzed by Titanium Silicalite", Journal of Catalysis, vol. 129, pp. 159-167, (1991).
J.A. Martens et al., "The potential and limitations of the n-decane hydroconversion as a test reaction for characterization of the void space of molecular sieve zeolites", Zeolites, vol. 6, pp. 334-348, (1986).
P. Wu et al., "Singular catalytic properties fo Ti-MWW in the selective oxidation of alkanes" Stud. Surf. Sci. Catal., 135:165 (2001).

* cited by examiner

*Primary Examiner*—Janet L Andres
*Assistant Examiner*—David E Gallis
(74) *Attorney, Agent, or Firm*—Panitch Schwarze Belisario & Nadel LLP

(57) ABSTRACT

A process for producing propylene oxide, includes the steps of reacting propylene with hydrogen peroxide in the presence of a crystalline titanosilicate catalyst having a pore structure of a 12-oxygen-membered ring or more in an organic solvent as a medium capable of being separated from water solution, obtaining a reaction mixture containing propylene oxide, separating the reaction mixture into liquid phases to obtain a water layer and an oil layer containing the organic solvent, the propylene oxide thereby being separated from the water into the oil layer.

4 Claims, No Drawings

PROCESS FOR PRODUCING PROPYLENE OXIDE

CROSS REFERENCE TO RELATED APPLICATION

This application is a Section 371 of International Application No. PCT/JP2004/002757, filed Mar. 4,2004, which was published in the Japanese language on Sep. 16, 2004, under International Publication No. WO 2004/078739 A1, the disclosure of which is incorporated herein by reference.

TECHNICAL FIELD

The present invention relates to a process for producing propylene oxide characterized by epoxidizing propylene with hydrogen peroxide in the presence of a crystalline titanosilicate catalyst.

BACKGROUND

As a technique for producing propylene oxide by carrying out an epoxidation reaction of propylene with hydrogen peroxide in the presence of a crystalline titanosilicate catalyst, a method of using a TS-1 catalyst has been known and it has been well known that a methanol solvent is preferred in that case (for example, Journal of Catalysis 129, 159, (1991)). In order to obtain propylene oxide from the reaction mixture, however, propylene oxide must be separated by distillation from water and a methanol solvent, and additionally in order to recover the methanol solvent, water and methanol must be separated by distillation, which had a problem in that a huge amount of energy was required. Further, methanol and water were known to readily react with propylene oxide to produce methoxypropanol and propylene glycol, and hence there was a concern about a loss of propylene oxide. There was disclosed a process, therefore, (for example, in WO99/14208) in which the desired epoxy compound is separated from water solution by liquid-liquid extraction from a reaction mixture obtained by using a TS-1 catalyst and a methanol solvent with the use of an organic solvent capable of being separated from water solution. Since, however, another extraction solvent, which was different from the reaction solvent, was used in this process, there was a problem in that complicated steps such as distillation separation of two organic solvents and purification of each of the solvents by distillation were required. When the methanol solvent was not used, complicated steps were unnecessary but high activity was not attained.

Also, there were known processes using a Ti-MWW catalyst and an organic solvent such as methanol, acetone, acetonitrile or the like that can be completely mixed with water, and it was known that the acetonitrile solvent was preferred in that case and high activity was obtained as compared with the case of using a TS-1 catalyst and a methanol solvent (for example, 2001-fiscal year Next-generation Chemical Process Technical Development/Nonhalogen Chemical Process Technical Development Progress Report, 168-210, (2002)). However, there was a problem in that produced water and the solvent must be separated, and industrial distillation separation was huge energy consuming.

DETAILED DISCLOSURE OF THE INVENTION

An object of the present invention is to provide a process for producing propylene oxide characterized by reacting propylene with hydrogen peroxide in the presence of a crystalline titanosilicate catalyst, which process is industrially superior in that the reaction can be conducted with high efficiency, and the product and a solvent can be readily recovered from the reaction mixture.

That is, the present invention relates to a process for propylene oxide, which process comprises reacting propylene with hydrogen peroxide in the presence of a crystalline titanosilicate catalyst having a pore structure of a 12-oxygen-membered ring or more, utilizing an organic solvent as a medium capable of being separated from water solution, obtaining a reaction mixture containing propylene oxide, and separating the reaction mixture into liquid phases to obtain a water layer, and an oil layer containing the organic solvent, thereby the propylene oxide being separated from the water into the oil layer.

BEST MODE FOR CARRYING OUT THE INVENTION

The present invention employs crystalline titanosilicate having a pore structure of a 12-oxygen-membered ring or more as a catalyst. Crystalline titanosilicate is titanosilicate having a zeolite structure. Typical examples of crystalline titanosilicate having a pore structure of a 12-oxygen-membered ring or more include crystalline titanosilicate having an MTW structure (Ti-ZSM-12) according to the structural codes of International Zeolite Association, crystalline titanosilicate having a BEA structure (Ti-β), crystalline titanosilicate having an MWW structure (Ti-MWW) and crystalline titanosilicate having a DON structure (Ti-UTD-1). Among the above-mentioned crystalline titanosilicates, it is clarified by International Zeolite Association that Ti-ZSM-12, Ti-β and Ti-MWW have a pore structure of a 12-oxygen-membered ring, and Ti-UTD-1 has a pore structure of a 14-oxygen-membered ring. A pore structure of a 12-oxygen-membered ring or more in the present invention means a pore structure of which entry port has a pore of a 12-oxygen-membered ring or more, and the size of an entry port of the pore is important for the reaction of propylene and hydrogen peroxide in the present invention.

Among the above-mentioned crystalline titanosilicates, the Ti-MWW catalyst can be used particularly preferably because of enhanced reactivity of propylene and hydrogen peroxide in the presence of an organic solvent capable of being separated from liquid water. In addition, a silylated Ti-MWW catalyst can be used particularly preferably since higher reactivity can be obtained by treating the TI-MWW catalyst with a silylating reagent.

The crystalline titanosilicate catalyst having a pore structure of a 12-oxygen-membered ring to be used in the present invention is used in the form of powder or a molded product in accordance with a reaction method. A fixed bed flow reaction method or a slurry reaction method is generally adopted as a reaction method.

In the present invention, the reaction of propylene with hydrogen peroxide is performed in the presence of an organic solvent capable of being separated from water solution. The organic solvent capable of being separated from water solution in the present invention means an organic solvent that forms two liquid layers when mixed with water at a temperature of 20° C., and it is preferably a single solvent in view of separation, but may be a mixture of solvents. Preferred organic solvent is a substantially inert compound in the reaction. Suitably used are hydrocarbon, halogenated hydrocarbon, a nitrile compound, a ketone compound and an ether compound. Specific examples thereof include hexane, heptane, benzene, toluene, xylene, ethylenedichloride, chlorobenzene, propionitrile, methyl ethyl ketone, methyl isobutyl ketone and dibutyl ether. The organic solvent may be a mixture with an organic compound except hydrocarbon, halogenated hydrocarbon, a nitrile compound, a ketone compound and an ether compound. The organic solvent may be a mixture of an organic compound other than the hydrocarbon, halogenated-hydrocarbon, the nitrile compound, the ketone compound. The organic solvent is preferably a compound having a higher boiling point than propylene oxide for the purpose of facilitating separation by distillation from propylene oxide.

In the case of an epoxidation reaction of propylene with hydrogen peroxide, the organic solvent capable of being separated from water solution is always used in the presence of water, because water is co-produced in the reaction. In addition to the water produced by the reaction, water is generally recycled from a separation step or purification step or other steps. In the case of using hydrogen peroxide previously manufactured, water is generally supplied as aqueous hydrogen peroxide together with hydrogen peroxide.

The epoxidation reaction can be performed at a temperature of typically 0 to 150° C., preferably 20 to 100° C. Reaction pressure is typically 0.1 to 20 MPa, preferably 0.3 to 10 MPa.

A method of supplying hydrogen peroxide is not particularly limited, but includes a method of supplying aqueous hydrogen peroxide previously manufactured and a method of supplying hydrogen peroxide synthesized in-situ from hydrogen and oxygen. In the case of using hydrogen peroxide previously manufactured, the quantity of propylene to be fed with respect to hydrogen peroxide is typically 1 to 200 moles per mol of hydrogen peroxide (propylene/hydrogen peroxide), preferably 1.1 to 100 moles.

Unreacted propylene after the reaction is typically used as a material for an epoxidation reaction through recycling after separation purification. The use of the organic solvent capable of being separated from water solution allows oil/water separation of the reaction mixture into two layers of a water layer and an oil layer. The recovery of propylene oxide and the organic solvent can easily be performed by the oil/water separation. Both propylene oxide and an organic solvent can easily be recovered from an oil layer containing primarily the organic solvent and propylene oxide, for example, by ordinary distillation separation. Valuable compounds such as propylene, propylene oxide and a solvent dissolved in a water layer can be recovered from a water layer by liquid-liquid extraction and distilled separation. A method of recovering by liquid-liquid extraction is preferable because of no loss of propylene oxide and no energy loss by distillation. An extraction solvent to be used for liquid-liquid extraction is not particularly limited as long as the active ingredients can be extracted; also an organic solvent used in the above-mentioned reaction is preferably used since the separation recovery of the solvent is easy.

EXAMPLES

The present invention is specifically described hereinafter by examples.

Example 1

A reaction was performed by using a Ti-MWW catalyst such that Ti content by ICP-OES analysis was 1.1% by weight, which was prepared in accordance with a method described in Chemistry Letters 774, (2000). That is, a solution of $H_2O_2$: 5% by weight, water: 47.5% by weight and propionitrile: 47.5% by weight was prepared by using a 36% aqueous solution of $H_2O_2$, propionitrile and pure water. 12 g of the prepared solution and 0.010 g of the pulverized Ti-MWW catalyst were charged into a 50-ml stainless-steel autoclave. The charged solution was separated into two layers. Next, the autoclave was moved onto an ice bath, and 10 g of liquefied propylene was charged into the autoclave, which was further pressurized to 2 MPa-G with nitrogen. The autoclave was put in a block bath made of aluminum at a temperature of 40° C. to perform a reaction at a temperature of 40° C. After 5 minutes, when the interior temperature became approximately 35° C., the reaction was regarded as initiated. In 1 hour after the reaction initiation, the autoclave was taken out of the block bath. The autoclave was cooled with ice and depressurized while gas was absorbed in acetonitrile to thereafter take out a reaction solution. Acetonitrile was added to the obtained reaction solution to make a uniform solution. Analysis was performed by using gas chromatography for each of acetonitrile in which gas was absorbed and the uniform reaction solution with the addition of acetonitrile. As a result, propylene oxide producing activity per catalyst weight was 0.370 $mol \cdot h^{-1} \cdot g^{-1}$.

A reaction was performed again under the same conditions to obtain a reaction solution in the same manner. The catalyst was removed from the obtained reaction solution, which was left standing. The reaction solution was separated into two liquid layers. After standing, the reaction solution was separated to recover 6.3 g of a water layer and 5.4 g of an oil layer. As a result of analyzing each of the layers by gas chromatography, the partition ratio of propylene oxide between the water layer and the oil layer was 0.21/0.79.

Example 2

A reaction and analysis were performed in the same manner as Example 1 except for replacing propionitrile with 1,2-dichloroethane. As a result of the analysis, propylene oxide producing activity per catalyst weight was 0.272 $mol \cdot h^{-1} \cdot g^{-1}$. A solution employing 1,2-dichloroethane was also separated into two solution layers in the same manner as Example 1.

A reaction was performed again under the same conditions to obtain a reaction solution in the same manner. The catalyst was removed from the obtained reaction solution, which was left standing. The reaction solution was separated into two solution layers. After standing, the reaction solution was separated to recover 6.1 g of a water layer and 5.4 g of an oil layer. As a result of analyzing each of the layers by gas chromatography, the partition ratio of propylene oxide between the water layer and the oil layer was 0.23/0.77.

Example 3

A Ti-MWW catalyst used in Example 1 was silylated to prepare a silylated Ti-MWW catalyst. That is, 3.4 g of 1,1,1,3,3,3-hexamethyldisilazane, 50 g of toluene and 5 g of a Ti-MWW catalyst were mixed and refluxed for 1.5 hours to thereby perform silylation. In addition, after being filtered out and washed, the mixture was dried under reduced pressure at a temperature of 120° C. to obtain the silylated Ti-MWW catalyst. A reaction and analysis were performed in the same manner as Example 1 with the obtained silylated Ti-MWW catalyst and propionitrile as a solvent. As a result of the analysis, propylene oxide producing activity per catalyst weight was 0.489 $mol \cdot h^{-1} \cdot g^{-1}$.

Example 4

A reaction and analysis were performed by using 1,2-dichloroethane as a solvent in the same manner as Example 2 except for using the silylated Ti-MWW catalyst used in Example 3. A solution after the reaction was also separated into two solution layers in the same manner as Example 2. As a result of the analysis, propylene oxide producing activity per catalyst weight was 0.594 mol·h$^{-1}$·g$^{-1}$.

Comparative Example 1

A reaction and analysis were performed by using propionitrile as a solvent in the same manner as Example 1 except for replacing the Ti-MWW catalyst with a TS-1 catalyst having a pore structure of a 10-oxygen-membered ring and Ti content of 1.3% by weight by ICP-OES analysis. As a result of the analysis, propylene oxide producing activity per catalyst weight was 0.0101 mol·h$^{-1}$·g$^{-1}$.

Comparative Example 2

A reaction and analysis were performed by using 1,2-dichloroethane as a solvent in the same manner as Example 2 except for replacing the Ti-MWW catalyst with a TS-1 catalyst having a pore structure of a 10-oxygen-membered ring that was used in Comparative Example 1. As a result of the analysis, propylene oxide producing activity per catalyst weight was 0.0464 mol·h$^{-1}$·g$^{-1}$.

Comparative Example 3

A reaction and analysis were performed by using the Ti-MWW catalyst in the same manner as Example 1 except for replacing propionitrile with acetonitrile. As a result of the analysis, propylene oxide producing activity per catalyst weight was 0.393 mol·h$^{-1}$·g$^{-1}$. However, the obtained reaction solution was uniform and separable.

Comparative Example 4

A reaction and analysis were performed in the same manner as Example 1 except for replacing propionitrile with methanol and replacing the Ti-MWW catalyst with the TS-1 catalyst used in Comparative Example 1. As a result of the analysis, propylene oxide producing activity per catalyst weight was 0.165 mol·h$^{-1}$·g$^{-1}$. The obtained reaction solution was uniform and not separable.

INDUSTRIAL APPLICABILITY

As described above, the present invention can provide a process for producing propylene oxide by reacting propylene with hydrogen peroxide in the presence of a crystalline titanosilicate catalyst, which process is highly efficient and enables easy recovery of the product and the solvent from the reaction mixture.

The invention claimed is:

1. A process for producing propylene oxide, which process comprises
   reacting propylene with hydrogen peroxide in the presence of a crystalline titanosilicate catalyst having a pore structure of a 12-oxygen-membered ring or more, utilizing an organic solvent as a medium capable of being separated from water solution,
   obtaining a reaction mixture containing propylene oxide and
   separating the reaction mixture into liquid phases to obtain a water layer, and an oil layer containing the organic solvent, thereby the propylene oxide being separated from the water into the oil layer.

2. A process according to claim 1, wherein the catalyst is a crystalline titanosilicate catalyst having a MWW structure.

3. A process according to claim 1, wherein the organic solvent is an organic solvent capable of being separated from water solution and is selected from the group consisting of hydrocarbon, halogenated hydrocarbon, a nitrile compound, a ketone compound and an ether compound.

4. A process according to claim 2, wherein the organic solvent is an organic solvent capable of being separated from water solution and is selected from the group consisting of hydrocarbon, halogenated hydrocarbon, a nitrile compound, a ketone compound and an ether compound.

* * * * *